US 8,295,565 B2

(12) United States Patent
Gu et al.

(10) Patent No.: US 8,295,565 B2
(45) Date of Patent: Oct. 23, 2012

(54) METHOD OF IMAGE QUALITY ASSESSMENT TO PRODUCE STANDARDIZED IMAGING DATA

(75) Inventors: Jia Gu, Shenzhen (CN); Wenjing Li, Fremont, CA (US)

(73) Assignee: STI Medical Systems, LLC, La Jolla, CA (US)

( * ) Notice: Subject to any disclaimer, the term of this patent is extended or adjusted under 35 U.S.C. 154(b) by 1234 days.

(21) Appl. No.: 12/075,910

(22) Filed: Mar. 14, 2008

(65) Prior Publication Data

US 2008/0226148 A1 Sep. 18, 2008

Related U.S. Application Data

(60) Provisional application No. 60/918,527, filed on Mar. 16, 2007.

(51) Int. Cl.
*G06K 9/00* (2006.01)
*G06K 9/36* (2006.01)
*G06K 9/40* (2006.01)

(52) U.S. Cl. ........ 382/128; 382/286; 382/255; 382/190; 382/162; 382/168

(58) Field of Classification Search .......................... None
See application file for complete search history.

(56) References Cited

U.S. PATENT DOCUMENTS

| 6,081,612 A * | 6/2000 | Gutkowicz-Krusin et al. ................. 382/128 |
| 6,738,494 B1 * | 5/2004 | Savakis et al. ................ 382/100 |
| 7,711,174 B2 * | 5/2010 | Sammak et al. ................ 382/133 |
| 7,940,970 B2 * | 5/2011 | Levanon et al. ............... 382/128 |
| 2003/0095197 A1 * | 5/2003 | Wheeler et al. ............... 348/241 |
| 2004/0156559 A1 * | 8/2004 | Cheng et al. .................. 382/286 |
| 2006/0147125 A1 * | 7/2006 | Caviedes ....................... 382/266 |
| 2006/0159325 A1 * | 7/2006 | Zeineh et al. ................. 382/128 |

OTHER PUBLICATIONS

Jia et al, "Automatic Image Quality Assessment for Uterine Cervical Imager", Medical Imaging 2006, Proc of SPIE vol. 6146 p. 61461B-1 to 61461 B-12.*
Nill et al (Objective Image quality measure derived from digital image power spectra, Optical engineering, Apr. 1992, vol. 31, 813-825).*

* cited by examiner

*Primary Examiner* — Jason M Repko
*Assistant Examiner* — Avinash J Yentrapati
(74) *Attorney, Agent, or Firm* — Martin E. Hsia

(57) ABSTRACT

Automated image quality assessment methods, which include locating a region of interest, region assessment, contrast assessment, blur assessment, and contaminant detection, on video data and high-resolution imagery. Where the blur assessment is performed without a reference image by dividing the region into non-overlapping block, measuring the wavenumber frequency of the blocks and calculating the ratio of the low frequency to high frequency areas.

11 Claims, 19 Drawing Sheets

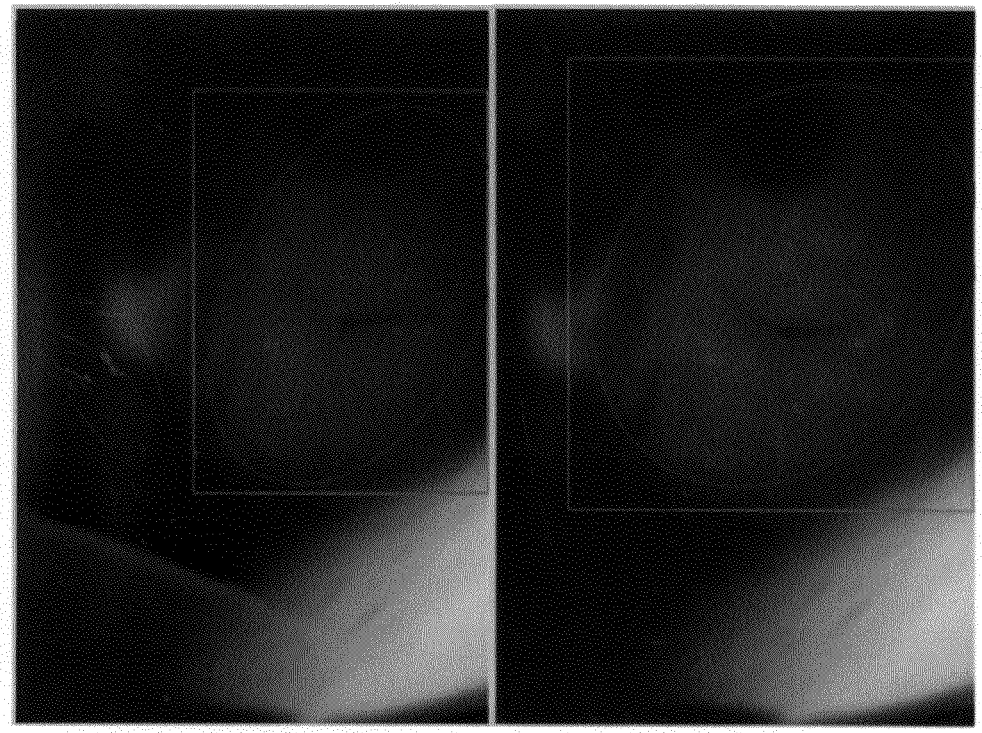
FIG 10(a)  FIG 10 (b)
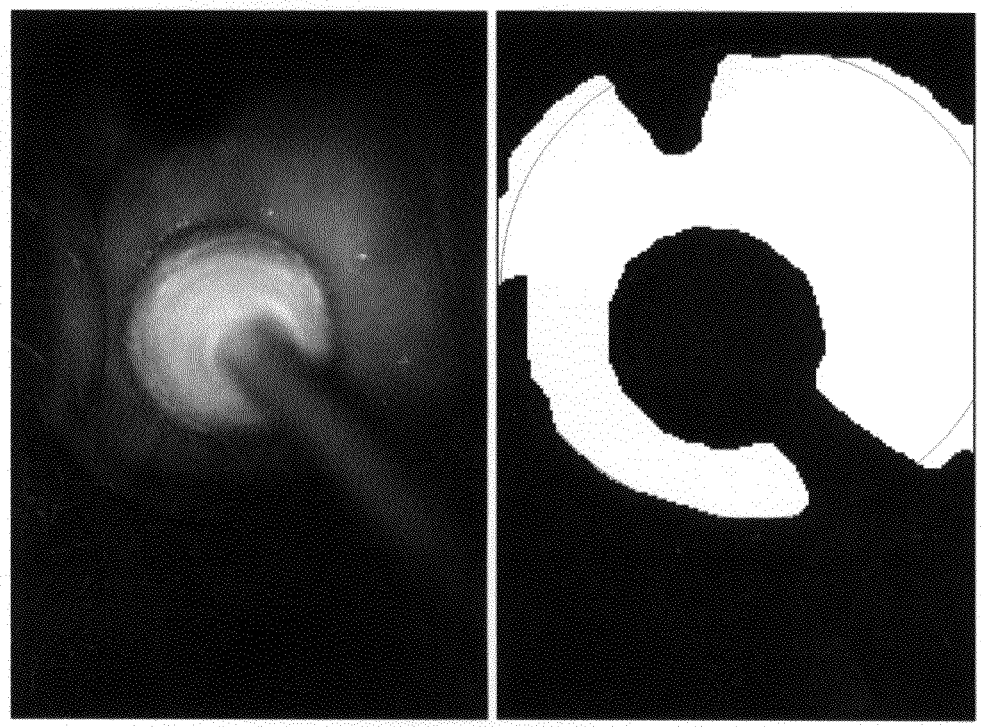
FIG 10(c)(1)  FIG 10(c)(2)

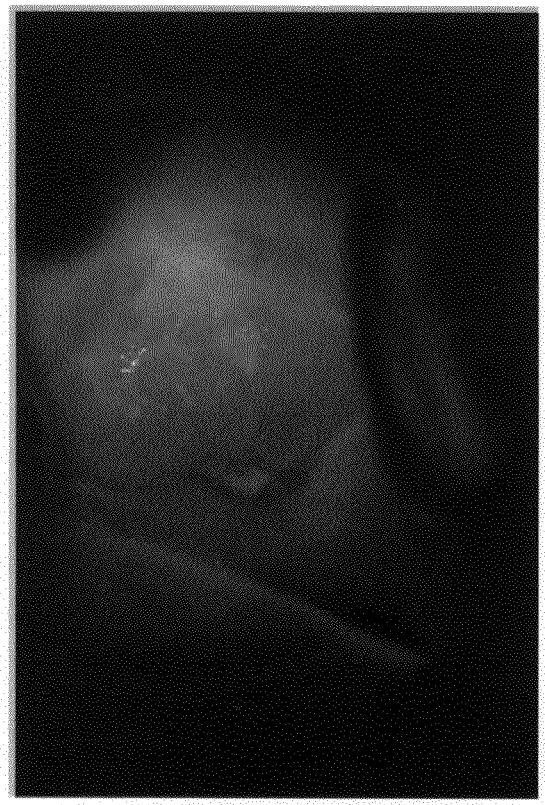 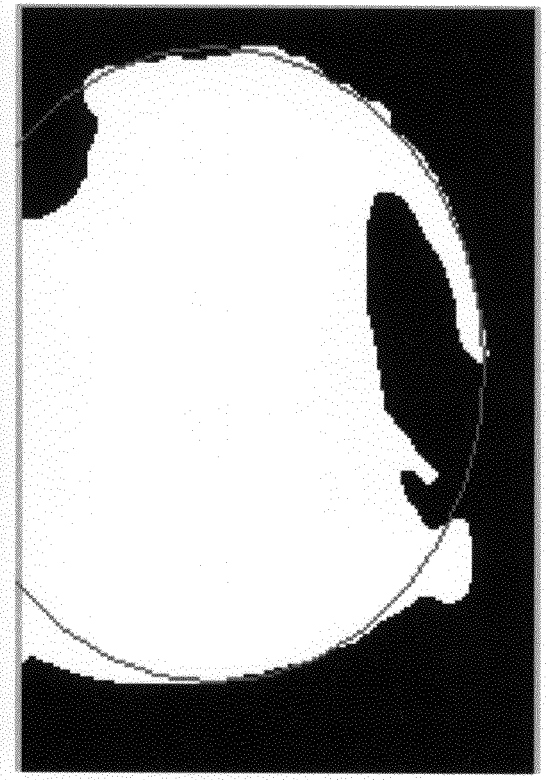
FIG 10(d)(1)   FIG 10(d)(2)
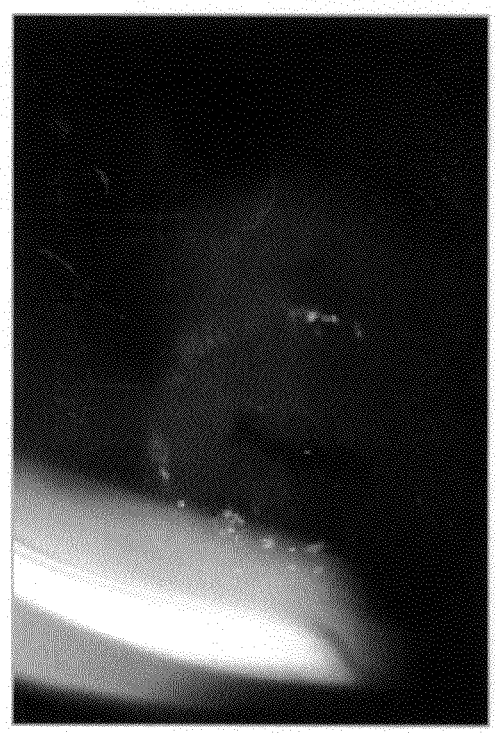 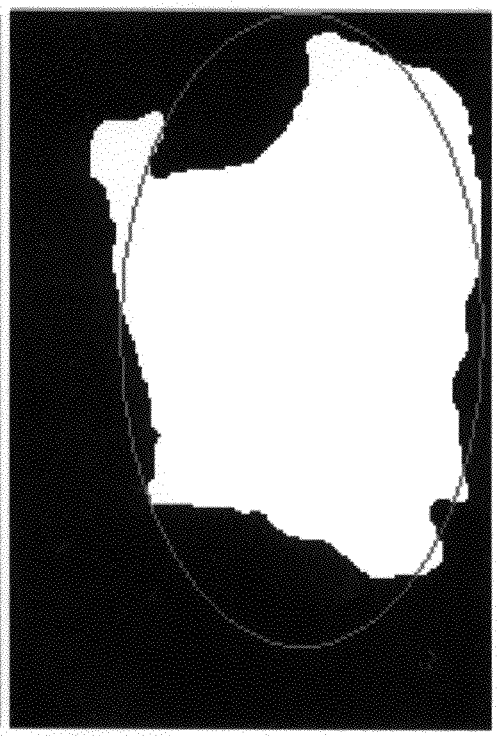
FIG 10 (e)(1)   FIG 10 (e)(2)

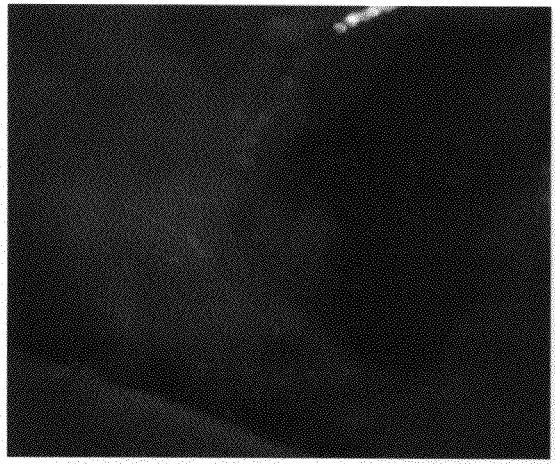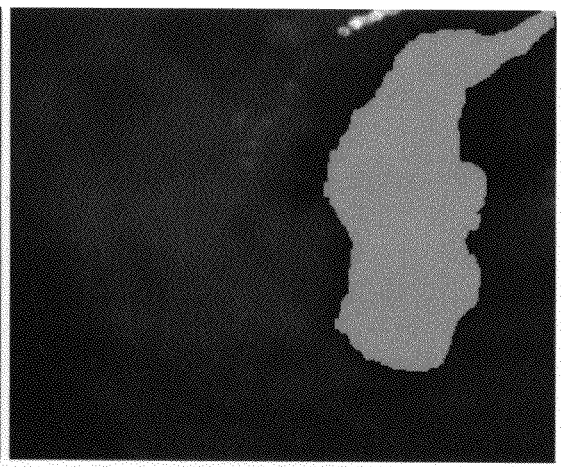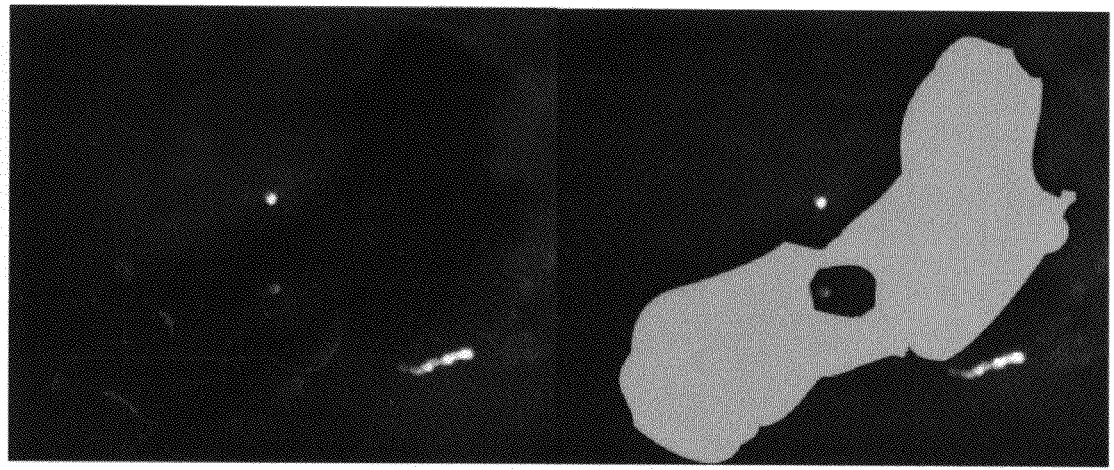
FIG 16(a)  FIG 16(b)  FIG 16(c)  FIG 16(d)

METHOD OF IMAGE QUALITY ASSESSMENT TO PRODUCE STANDARDIZED IMAGING DATA

This application claims priority to U.S. provisional patent application 60/918,527 filed on Mar. 16, 2007.

TECHNICAL FIELD

This invention generally relates to medical imaging and more specifically to image processing to achieve high-quality standardized digital imagery for use in archive-quality medical records and Computer-Aided-Diagnosis (CAD) systems.

BACKGROUND ART

Although this invention is being disclosed in connection with cervical cancer, it is applicable to many other areas of medicine. Uterine cervical cancer is the second most common cancer in women worldwide, with nearly 500,000 new cases and over 270,000 deaths annually (Globocan 2002 database, International agency for research in cancer, 2002, incorporated herein by reference). Colposcopy is a diagnostic method used to detect cancer precursors and cancer of the uterine cervix (B. S. Apgar, Brotzman, G. L. and Spitzer, M., Colposcopy: Principles and Practice, W.B. Saunders Company: Philadelphia, 2002, incorporated herein by reference). CAD for colposcopy represents a new application of medical image processing. The inventors have developed a CAD system that mimics or emulates the diagnostic process used by colposcopists to assess the severity of abnormalities (Lange H. and Ferris, Daron G.; Computer-Aided-Diagnosis (CAD) for colposcopy; SPIE Medical Imaging 2005; SPIE Proc. 5747, 2005, incorporated herein by reference). Scoring schemes, like the Reid's colposcopic index are an aid for making colposcopic diagnoses (Reid R, Scalzi P. Genital warts and cervical cancer. VII. An improved colposcopic index for differentiating benign papillomaviral infection from high-grade cervical intraepithelial neoplasia. Am J Obstet Gynecol 1985; 153:611-618, incorporated herein by reference) based on various features, including acetowhitening, vessel patterns and lesion margins. These features are individually assessed and scored before the scores of all features are combined to yield a composite score that grades disease severity. However, the quality of the images must be assessed before further analysis, to ensure reliable scoring. This invention includes a systematic framework of algorithms that automatically assesses cervical images acquired from a digital colposcope. This assessment results in a filtered dataset of images that can then be used for CAD algorithms. This invention can be used to control image acquisition, which guarantees quality of input imagery for CAD systems and archive-quality medical records, and can also be used in telemedicine cervical cancer diagnosis.

The limited quality of cervical imagery can be attributed to several factors, including: incorrect instrument settings, incorrect instrument positioning, glint, blur due to poor focus, and physical contaminants. Glint (specular reflection) eliminates the color information in affected pixels and can therefore introduce artifacts in feature extraction algorithms. Specular reflection is perfect, mirror-like reflection of light from a surface, in which light from a single incoming direction (a ray) is reflected into a single outgoing direction. A pixel is a single point in a graphic image and is the smallest single element of an image. Each pixel in an image has its own value that correlates to its brightness or intensity. In a color image, each pixel can be described using its hue, saturation, and value (HSV) or hue, saturation, lightness (HSL), but is usually represented instead as the red, green, and blue (RGB) intensities. Hue, saturation, and intensity (HSI) and hue, saturation, and brightness (HSB) are alternative names for HSV and HSL. HSL and HSV can be used to represent colors as points in a cylinder whose central axis ranges from black at the bottom to white at the top with neutral colors between them, where the angle around the axis corresponds to "hue", distance from the axis corresponds to "saturation", and distance along the axis corresponds to "lightness", "value", and "brightness". Instrument settings that result in an inadequate dynamic range (defined below) or overly constrained (too small) region of interest can reduce or eliminate pixel information and thus make image analysis algorithms unreliable. Poor focus causes image blur with a consequent loss of texture information. In addition, a variety of physical contaminants, such as blood, can obscure the desired scene, and reduce or eliminate diagnostic information from affected areas.

The present invention proposes a series of image quality assessment algorithms called Active Image Quality Assessment (AIQA), which include locating a region of interest, region assessment of the image, contrast assessment of the image, blur assessment of the image and contamination detection. These algorithms are specifically designed for cervical imaging, but can be applied to other types of tissue imaging as well. While many of the algorithms described herein are well-known in the art, the inventors are unaware of any other image processing method that uses the specific blur assessment algorithm of this invention, or its application to CAD technology. The following patents and patent applications may be considered relevant to the field of the invention:

U.S. Pat. No. 7,298,883 to Giger et al., incorporated herein by reference, discloses a computer-aided diagnosis (CAD) scheme to aid in the detection, characterization, diagnosis, and/or assessment of normal and diseased states (including lesions and/or images). The scheme employs lesion features for characterizing the lesion and includes a non-parametric classification, to aid in the development of CAD methods in a limited database scenario to distinguish between malignant and benign lesions. The non-parametric classification is robust to kernel size.

U.S. Pat. No. 7,272,252 to De La Torre-Bueno and McBride, incorporated herein by reference, discloses a method and apparatus for automated analysis of transmitted and fluorescently labeled biological samples, wherein the apparatus automatically scans at a low magnification to acquire images which are analyzed to determine candidate cell objects of interest. Once candidate objects of interest are identified, further analysis is conducted automatically to process and collect data from samples having different staining agents.

U.S. Patent Publication No. 2007/0019854 to Gholap; Abhijeet S. et al., incorporated herein by reference, discloses a method and system of automated digital image analysis of prostrate neoplasms using morphologic patterns. The method and system provide automated screening of prostate needle biopsy specimens in a digital image and automated diagnosis of prostatectomy specimens.

U.S. Patent Publication No. 2005/0251013 to Krishnan, et al., incorporated herein by reference, discloses systems and methods for processing a medical image to automatically identify the anatomy and view (or pose) from the medical image and automatically assess the diagnostic quality of the medical image. In one aspect a method for automated decision support for medical imaging includes obtaining image data, extracting feature data from the image data, and automatically performing anatomy identification, view identification and/or determining a diagnostic quality of the image data, using the extracted feature data.

U.S. Patent Publication No. 2005/0049497 to Krishnan, et al., incorporated herein by reference, discloses CAD (computer-aided diagnosis) systems and applications for breast imaging are provided, which implement methods to automatically extract and analyze features from a collection of patient information (including image data and/or non-image data) of a subject patient, to provide decision support for various aspects of physician workflow including, for example, automated diagnosis of breast cancer other automated decision support functions that enable decision support for, e.g., screening and staging for breast cancer. The CAD systems implement machine-learning techniques that use a set of training data obtained (learned) from a database of labeled patient cases in one or more relevant clinical domains and/or expert interpretations of such data to enable the CAD systems to "learn" to analyze patient data and make proper diagnostic assessments and decisions for assisting physician workflow.

U.S. Pat. No. 6,813,374 to Karimi et al., incorporated herein by reference, discloses a method and apparatus to assess the image quality of a CT scanner and verify that a CT scanner meets it is performance specifications.

U.S. Pat. No. 6,687,329 to Hsieh et al. discloses a method for processing image data comprising: (a) acquiring first image data via an imaging system; (b) processing the first image data in accordance with a CAD algorithm, the CAD algorithm performing at least one of segmenting, identifying and classifying a feature of interest in the first image data; and (c) prescribing acquisition of at least second image data based upon results of the CAD algorithm.

U.S. Patent Publication No. 2004/006,8167 to Hsieh, Jiang et al., incorporated herein by reference, discloses a method and system for generating processing image data based on the analysis of an initial image by a CAD algorithm which may perform various analyses such as segmentation, edge and structure identification. The post-processing may enhance a feature of interest in the image as identified by the CAD analysis. Image enhancement may include highlighting a feature of interest and changing the spatial resolution (e.g. zoom).

U.S. Pat. No. 6,147,705 to Krauter et al., incorporated herein by reference, discloses an apparatus and method for a video colposcope with electronic green filter. A video camera obtains a subject electronic image of a subject object, and using algorithm-driven digital signal processing circuitry (DSP), color saturation, hue, and intensity levels of the subject electronic image are modified according to DSP reference filter algorithm and reference color balance levels as stored, thus producing a modified electronic image corresponding to the subject electronic image. The modified electronic image is outputted to a display in continuous real time as the corresponding subject image is obtained by the video camera. This modified electronic image emulates that obtained through an optical green filter and incorporates a simulated white balance.

U.S. Pat. No. 5,982,917 to Clarke, et al., incorporated herein by reference, discloses a computer-assisted diagnostic (CAD) method and apparatus are described for the enhancement and detection of suspicious regions in digital X-ray images, with particular emphasis on early cancer detection using digital mammography. One objective is to improve the sensitivity of detection of suspicious areas such as masses, while maintaining a low false positive detection rate, and to classify masses as benign or malignant. A modular CAD technique has been developed as a potentially automatic and/or second-opinion method for mass detection and classification in digital mammography that may in turn be readily modified for application with different digital X-ray detectors with varying gray-scale and resolution characteristics. The method consists of using a plurality of CAD modules to preprocess and enhance image features in the gray-level, the directional texture, and the morphological domains.

U.S. Pat. No. 5,740,801 to Branson, incorporated herein by reference, discloses a system for acquiring images during a medical procedure and using the acquired images which includes a storage device for storing, for each one of a plurality of users of the system, or for each one of a plurality of medical procedures, or for each one of a plurality of input or output devices, information that indicates one or more processing operations to be performed on images obtained by an input device. A system processor responds to an identity the user who is currently using the system by performing processing operations on the obtained images and applying the images to an output device based on the stored information that corresponds to the current user.

DISCLOSURE OF INVENTION

The present invention described herein and more fully below, consists of a system framework of assessment algorithms to produce standardized imaging data suitable for archive-quality electronic medical records and for CAD systems. First, glare free image data is collected using a digital imager. A region of interest is then located within the image using an image classification algorithm. Region assessment is applied to the located region of interest to evaluate instrument settings, preferably incorrect camera zooming, incorrect camera positioning, and the existence of any obstructions in the image. The region of interest is then assessed for proper contrast using a histogram-based algorithm. Next, a blur assessment is performed without the use of a reference image. The region of interest is divided into non-overlapping blocks. A local measurement is computed for each of the blocks based on frequency information using an image power spectrum to create two-dimensional display. The two dimensional display is then converted to a one-dimensional display that is separated into three corresponding areas: low frequency, high frequency and noise. The degree of blur for each of the blocks is then calculated as the ratio of the low-frequency to high frequency areas. The degree of blur is then used to determine if the block is a blurred block. The total percentage of blurred blocks in the image to determine if said image is blurry. Finally, the invention detects contamination (obstructions) in the image using a training stage and a classification algorithm.

BRIEF DESCRIPTION OF DRAWINGS

FIG. 3(a) is the original RGB image, FIG. 3(b) is the transformed hue image, and FIG. 3(c) is the histogram of hue values.

FIG. 4(a) is the histogram of shifted hue values and FIG. 4(b) is the shifted hue image.

FIG. 5(a)

shows an RGB color image after each red, green, and blue component is smoothed separately; FIG. 5(b) shows the corresponding hue image after each red, green, and blue component is smoothed separately; FIG. 5(c) shows the histogram of hue values of the RGB image before each red, green, and blue component is smoothed separately; FIG. 5(d) shows the histogram of the hue values of the RGB image after smoothing; FIG. 5(e) shows the histogram of hue values before the whole histogram itself is smoothed, FIG. 5(f) shows the histogram of hue values after the whole histogram itself is smoothed.

FIG. 7(a) Fitted Gaussian model (2 classes); FIG. 7(b) Segmentation result FIG. 8(a) Cervix region—obtained by classification, FIG. 8 (b) Cervix region—closed holes. FIG. 8(c) Cervix region—cleaned up small regions.

FIG. 10(a), FIG. 10(b), FIG. 10(c)(1), FIG. 10(c)(2), FIG. 10(d)(1), FIG. 10(d)(2), FIG. 10(e)(1) and FIG. 10(e)(2) show some results of region assessment: FIG. 10(a) Incorrect camera zooming (the cervical region is too small). FIG. 10(b) Incorrect camera positioning (the cervical region is not well centered). FIG. 10(c)-FIG. 10(e) show 3 examples of improper existence of obstacles or partial visible cervix region: FIG. 10(c)(1) and FIG. 10(c)(2) show the existence of a cotton swab; FIG. 10(d)(1) and FIG. 10(d)(2) show the existence of a speculum; FIG. 10(e)(1) and FIG. 10(e)(2) show the extraordinary strong illumination caused by an abnormal camera setting, which impaired the image visibility. All the 3 examples above indicate poor image quality and that the entire cervix region cannot be seen clearly.

FIG. 11(a) An example of good contrast image, and FIG. 11(b) its corresponding histogram in red (R) channel.

FIG. 12(a) Input image; FIG. 12(b) shows the corresponding histogram in R Channel (False peak exists)

FIG. 14(a) 2D display of image power spectrum; FIG. 14(b) Conversion of image power spectrum into 1D diagram.

FIG. 16(a), FIG. 16(b), FIG. 16(c) and FIG. 16(d) show 2 examples of contamination detection results: FIG. 16(a): A portion of cervical image; FIG. 16(b): Contamination detection (gray area) for the cervical image in FIG. 16(a); FIG. 16(c): A portion of cervical image; FIG. 16(d): Contamination detection (gray area) results for the image in FIG. 16(c).

BEST MODES FOR CARRYING OUT INVENTION

1. System Framework

The presently preferred embodiment of the invention described herein preferably starts from an RGB (Red-Green-Blue) color space image from a digital colposcope. The input image is a glare free RGB image of a uterine cervix. Glare free imagery can be obtained either by cross-polarized (XP) image acquisition or glare removal pre-processing (Lange H.; Automatic glare removal in reflectance imagery of the uterine cervix; SPIE Medical Imaging 2005; SPIE Proc. 5747, 2005, incorporated herein by reference).

Figure 1:
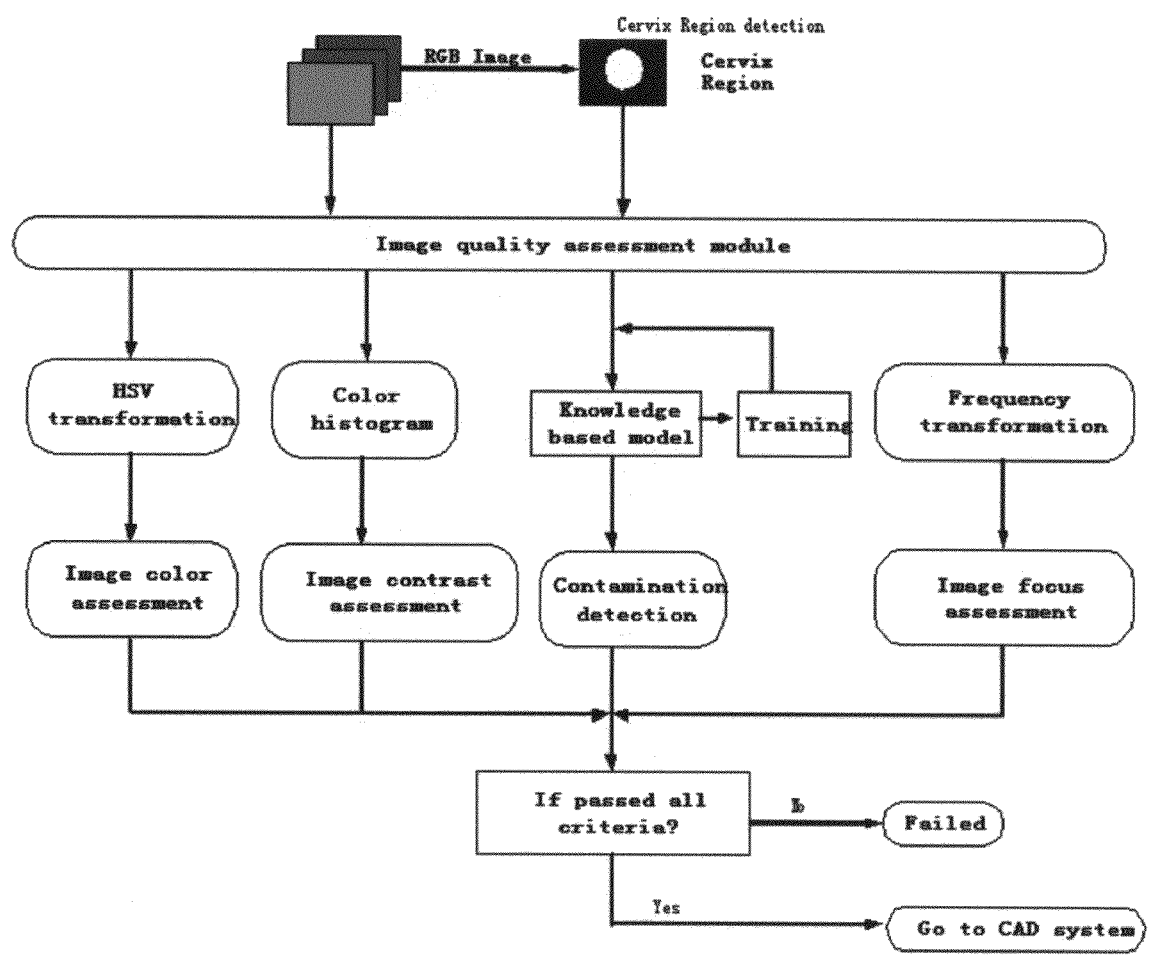
FIG. 1 shows the system framework of automatic image quality assessment algorithms.

The invention preferably comprises a framework of robust, real-time, industry-oriented algorithms to carry out the invention using statistical, morphological and signal processing methods. First, a Region-Of-Interest (ROI), preferably the cervix, is detected using a hue color cluster that discriminates between cervix and background. Then an adaptive peak-removing histogram equalization algorithm is used to assess the contrast. Following the contrast assessment, a frequency-based method is applied to fulfill the blur assessment. Finally, the contamination detection algorithm is accomplished by machine learning and a classification algorithm. The framework for the invention is shown in FIG. 1.

2. Region of Interest (ROI) Detection

Figure 2:
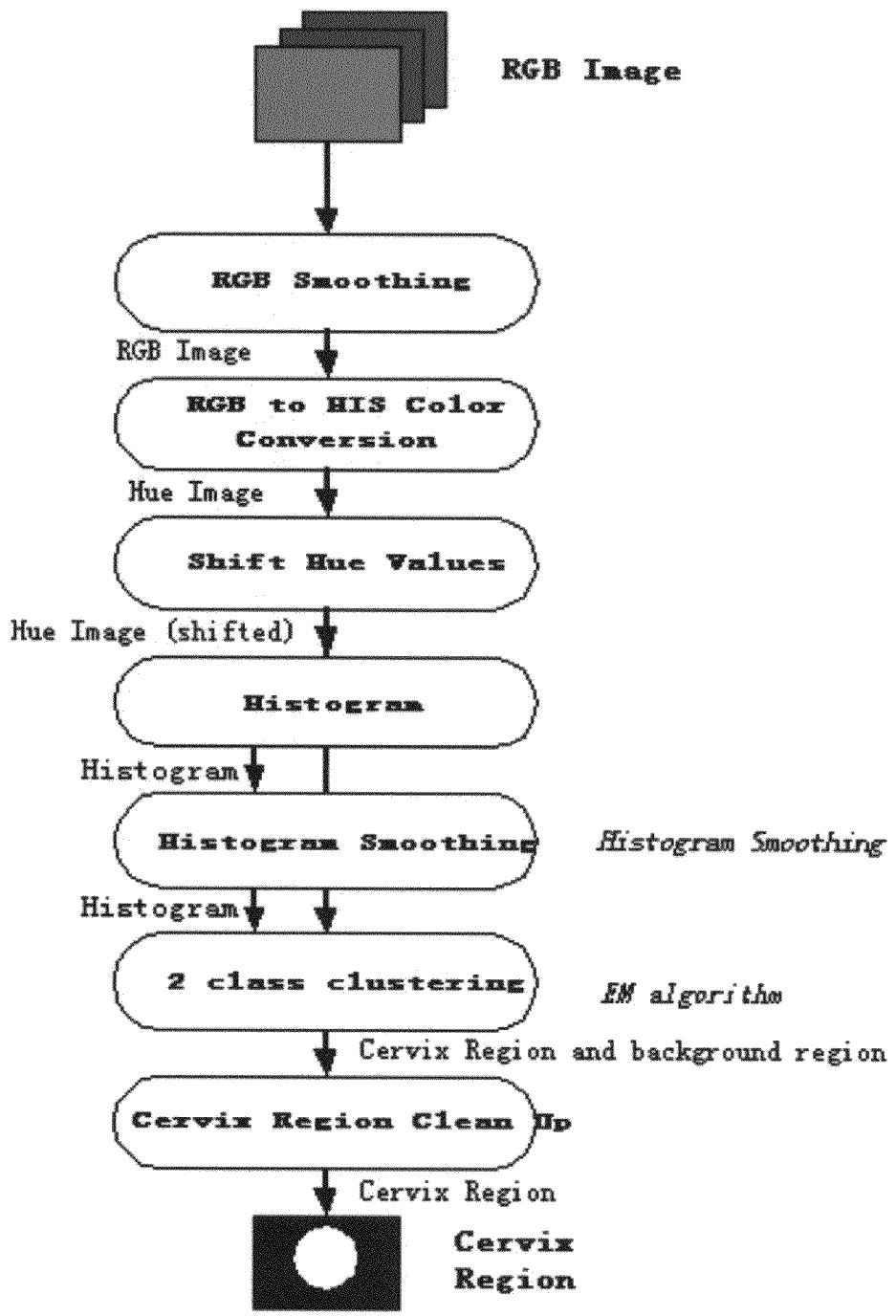
FIG. 2 shows the algorithm framework of probability based cervix region detection.

The ROI is detected using a hue color classifier that discriminates between the cervix and the background. First, the glare free RGB image is transformed into an HSI (Hue-Saturation-Intensity) image through HSI transformation. A histogram of the hue values is created and histogram smoothing is performed to reduce the inherent noise of the hue values. Then an Expectation-Maximization (EM) cluster is employed to fit the 2 Gaussian peaks in the histogram, and segmentation is performed based on the likelihood of a pixel belonging to one of the peaks. A Gaussian peak is the peak of a fitted curve, assuming that the histogram is an approximated Gaussian distribution (also known as a normal distribution). Segmentation refers to the process of partitioning a digital image into multiple regions (sets of pixels). The goal of segmentation is to simplify and/or change the representation of an image into something that is more meaningful and easier to analyze. An EM algorithm is used in statistics for finding maximum likelihood estimates of parameters in probabilistic models, where the model depends on unobserved latent variables. EM alternates between performing an expectation (E) step, which computes an expectation of the likelihood by including the latent variable as if they were observed, and a maximization (M) step, which computes the maximum likelihood estimates of the parameters by maximizing the expected likelihood found on the E step. The parameters found on the M step are then used to begin another E step, and the process is repeated. Once this is completed, post-processing on the ROI is performed. The ROI is then analyzed using region assessment and contrast assessment. The preferred algorithm framework of ROI detection is shown in FIG. 2.

The invention preferably uses a combination of various color-based algorithms. Those algorithms are supervised by a training algorithm in order to be directed specifically to the cervical tissue. In low-resolution image acquisition, a matching-filter algorithm to classify the image pixels into background and cervix, using a spectral angle of RGB space is employed. The algorithm first defines a target spectrum (corresponding the cervix) using a grid box sampling method. The target spectrum and all samples of spectra can be represented in multi-dimensional space. In this space, the red pixel value of a spectrum corresponds to the value in the red dimension, the green pixel value of a spectrum corresponds to the value in the green dimension, and the blue pixel value of a spectrum corresponds to the value in the blue dimension. The red, green, and blue values together define a vector in this space. The target spectrum and all samples of spectra can be represented as vectors this space. The spectral angle between the target spectrum vector and each sample spectrum vector can be assessed. Pixels for which this angle is less than some minimum threshold are deemed sufficiently similar to the cervical target pixels to pass filtering. In high-resolution image acquisition, a more accurate EM algorithm using HSV space is used.

The algorithm can be easily extended to alternate color spaces, such as LAB and LUV.

2.1 HSI Transformation

Figure 3A:
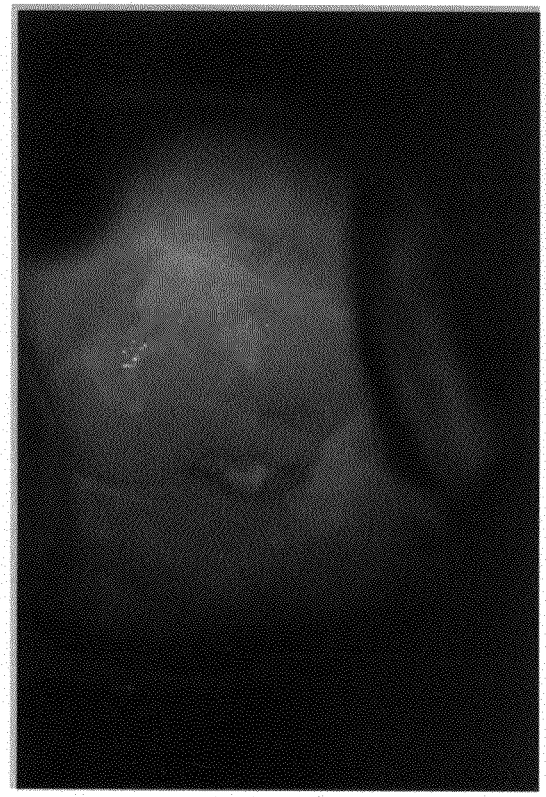
FIG. 3(a), FIG. 3(b) and FIG. 3(c) show the HSI transformation.
Figure 3B:
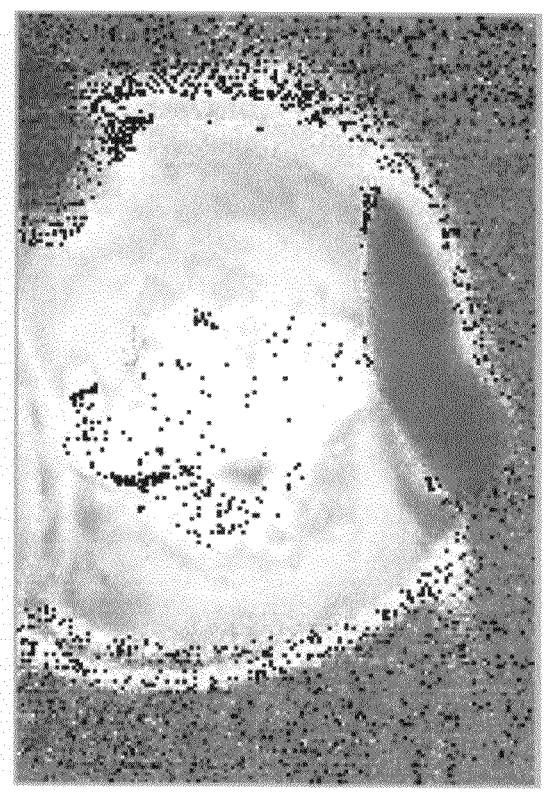
Figure 3C:
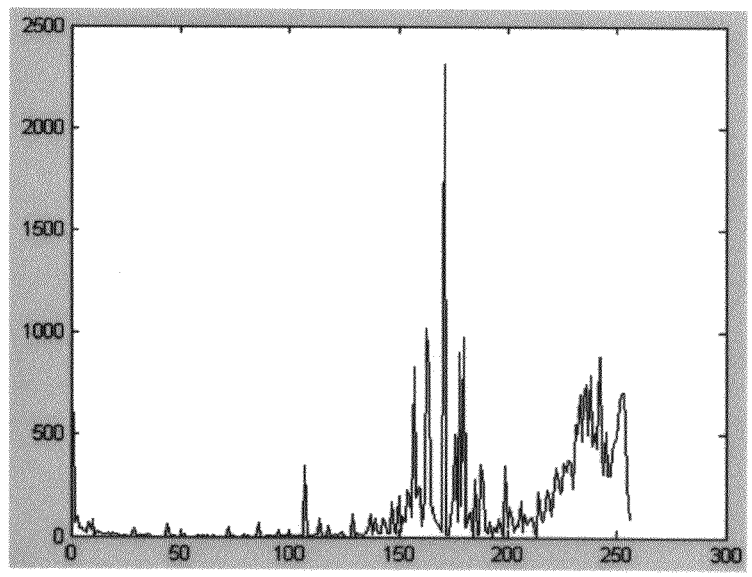

The hue color feature is used to characterize the color of the pixels. Preferably, the input RGB image is transformed from the RGB color space to the HSI color space, keeping the hue component for calculations. The original RGB image and transformed hue image are shown in FIG. 3(a) and FIG. 3(b) respectively. The hue values of interest are preferably located using a roll-over spectrum, which can easily be seen in the histogram of the hue values in FIG. 3(c). The roll-over spectrum is a technique used to generate the hue histogram. It involves shifting the phase of the histogram by 180 degrees.

Figure 4A:
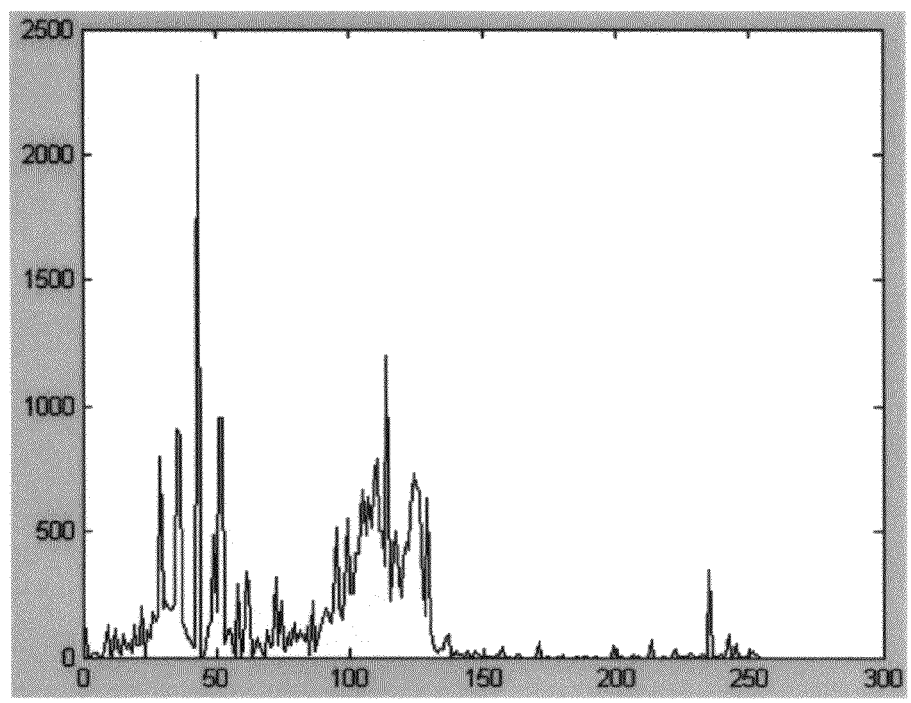
FIG. 4(a) and FIG. 4(b) show the hue shifting.
Figure 4B:
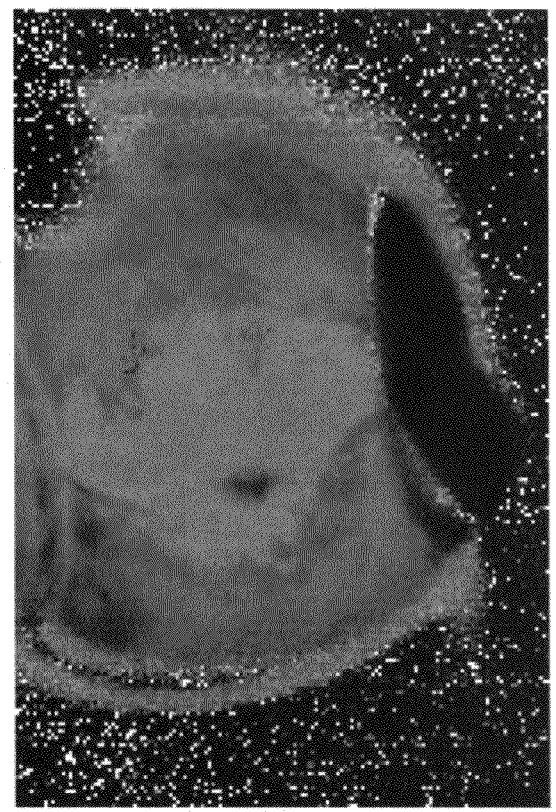

To simplify the calculations and visualization, all hue values are shifted by the median value (180 degrees) of the entire dynamic range of all hue values (360 degrees). The dynamic range is a term used to describe the ratio between the smallest and largest possible values of a variable quantity. The shifted histogram is shown in FIG. 4(a). As a reference, the red color now corresponds to the middle value of the hue channel. Color digital images are made of pixels, and pixels are made of combinations of primary colors. A channel in this context is the grayscale image of the same size as a color image, made of just one of these primary colors. For instance, an image from a standard digital camera will have a red, green and blue channel. A grayscale image has just one channel. FIG. 4(b) shows the shifted hue image.

2.2 Histogram Smoothing

The histogram of the hue values is inherently very noisy. Therefore, it is preferable to smooth the histogram. In image processing, it is usually necessary to perform noise reduction on an image before performing higher-level processing steps. Smoothers, or smoothing filters, are algorithms for time-series processing that reduce abrupt changes in the time-series and make it look smoother. Smoothers constitute a broad subclass of filters. Like all filters, smoothers may be subdivided into linear and nonlinear. Linear filters reduce the power of higher frequencies in the spectrum and preserve the power of lower frequencies For this invention, preferably the image in each R, G, B component is smoothed separately, with a 3×3 median filter followed by a 7×7 Gaussian filter with a sigma (the variance) of 1.5. The median filter is preferably a non-linear digital filtering technique, often used to remove noise from images or other signals. The Gaussian filter is preferably a linear filter that is also used as a smoother. The output of the Gaussian filter at the moment $\tau$ is the weighted mean of the input values, and the weights are defined by formula.

Figure 5A:
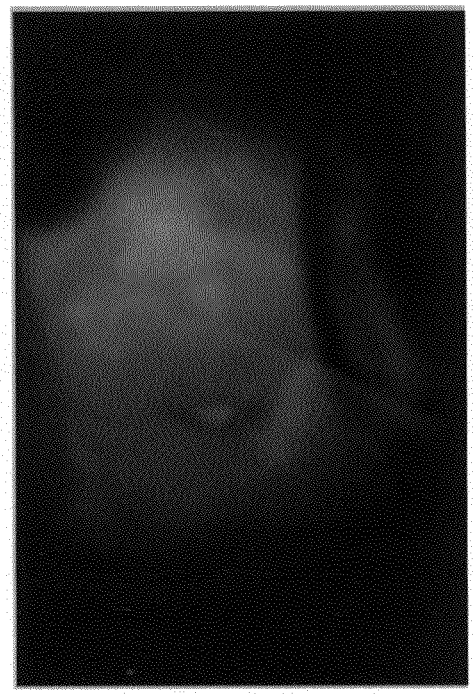
FIG. 5(a), FIG. 5(b), FIG. 5(c), FIG. 5(d), FIG. 5(e) and FIG. 5(f) show the histogram smoothing process.
Figure 5B:
Figure 5C:
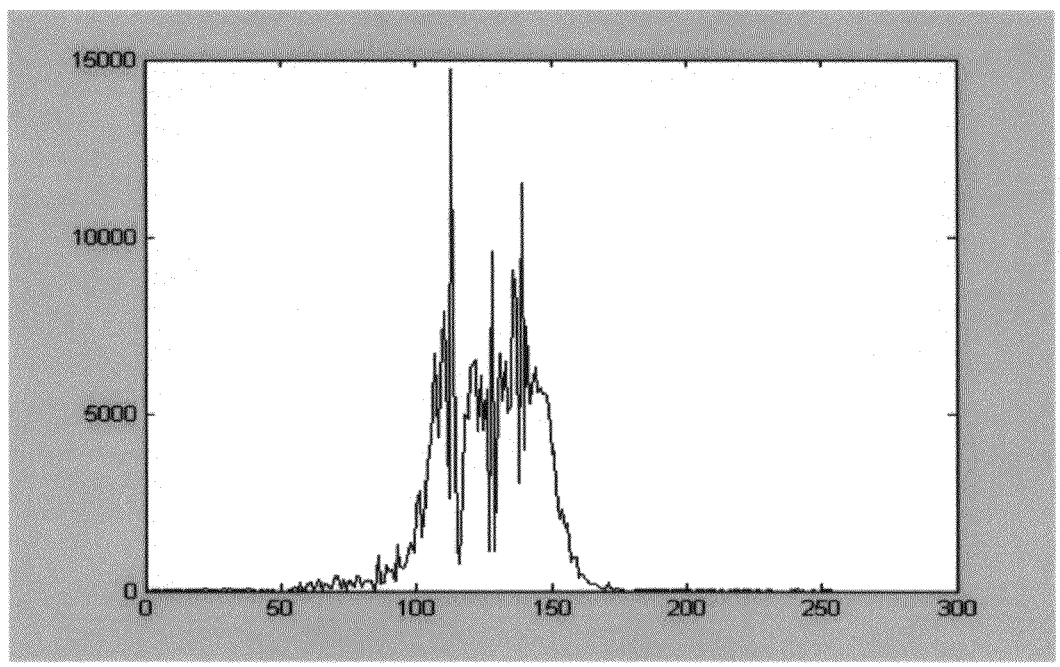
Figure 5D:
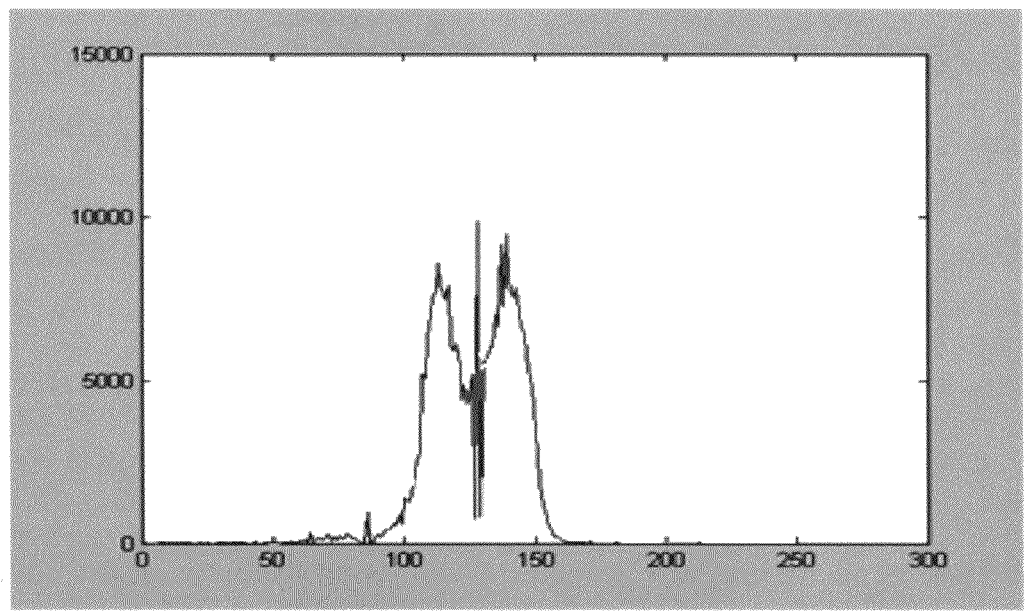
Figure 5E:
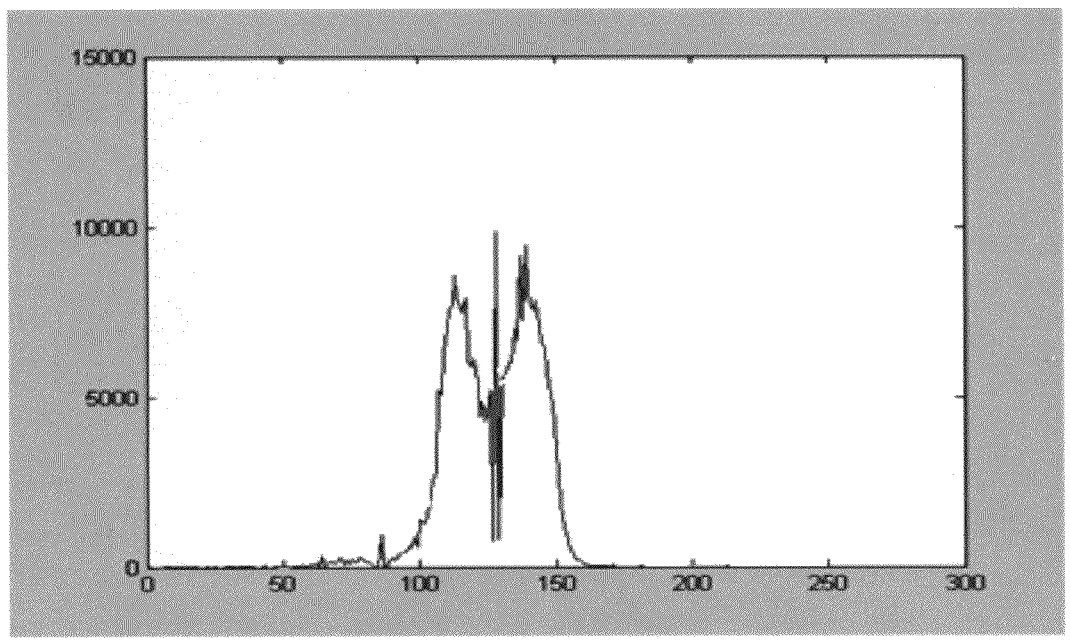
Figure 5F:
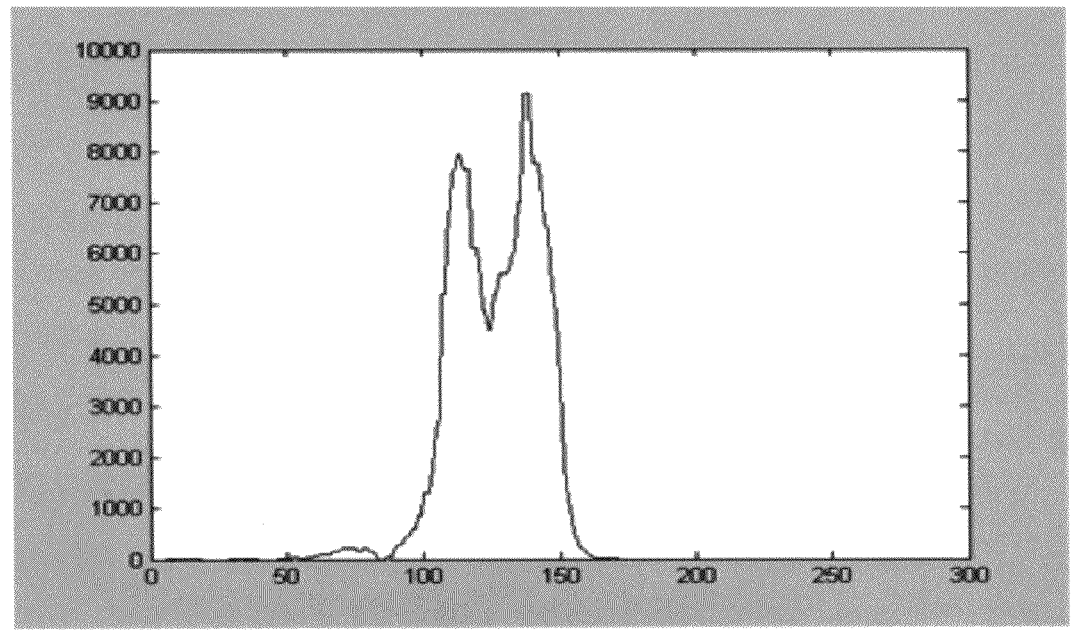

The results for the RGB color image, the hue characteristics image and the histogram before each R, G, B component is smoothed and after each R, G, B component is smoothed are shown in FIGS. 5(a), 5(b), 5(c), and 5(d) respectively. Next, the histogram itself is smoothed, preferably using an opening-closing Alternating Sequential Filter (ASF) with a horizontal line structuring element of size 2 (SDC Morphology Toolbox for MATLAB, Version 1.3 of 21 Apr. 2004, SDC Information Systems, Naperville, Ill., incorporated herein by reference). FIG. 5(e) shows the histogram before smoothing and FIG. 5(f) shows the histogram after smoothing.

2.3 Classification and Post-Processing

Figure 6:
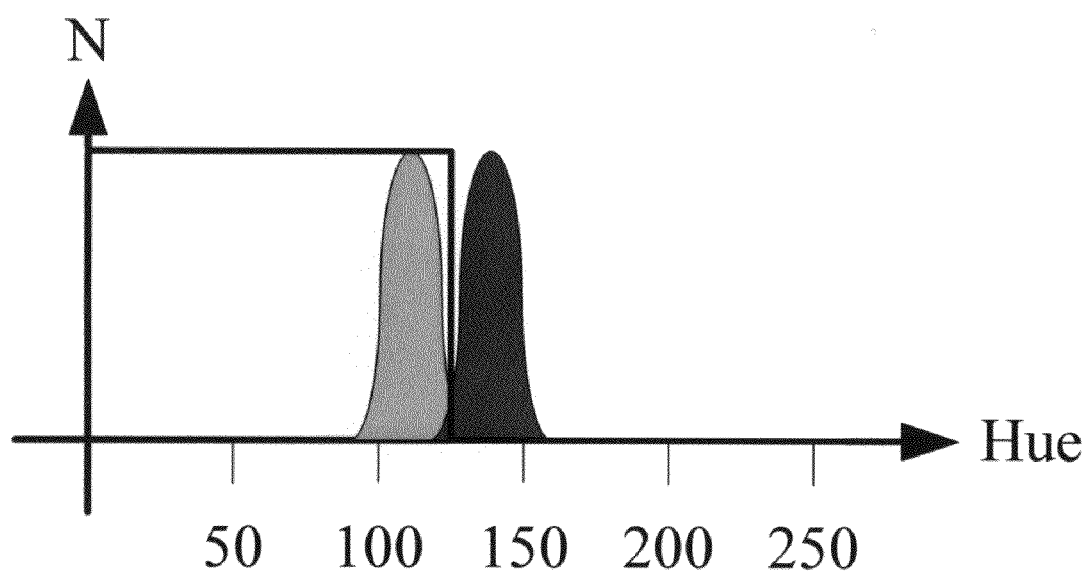
FIG. 6 shows the expected histogram of hue values wherein the histogram has a peak (light gray) in the region corresponding to the cervix and vaginal sidewalls, and a very close peak (dark gray) to the right of it when the body parts outside the cervix and vaginal sidewalls are visible.
Figure 7A:
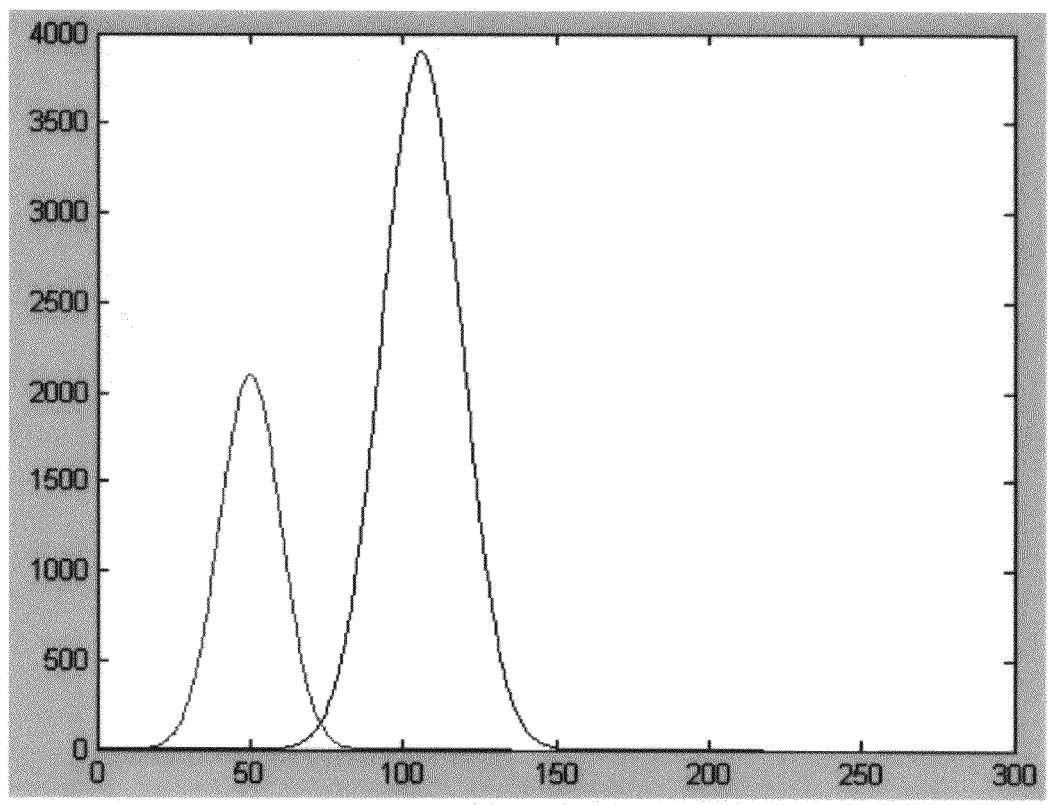
FIG. 7(a) and FIG. 7(b) shows the fitted Gaussian model and the classification result.
Figure 7B:
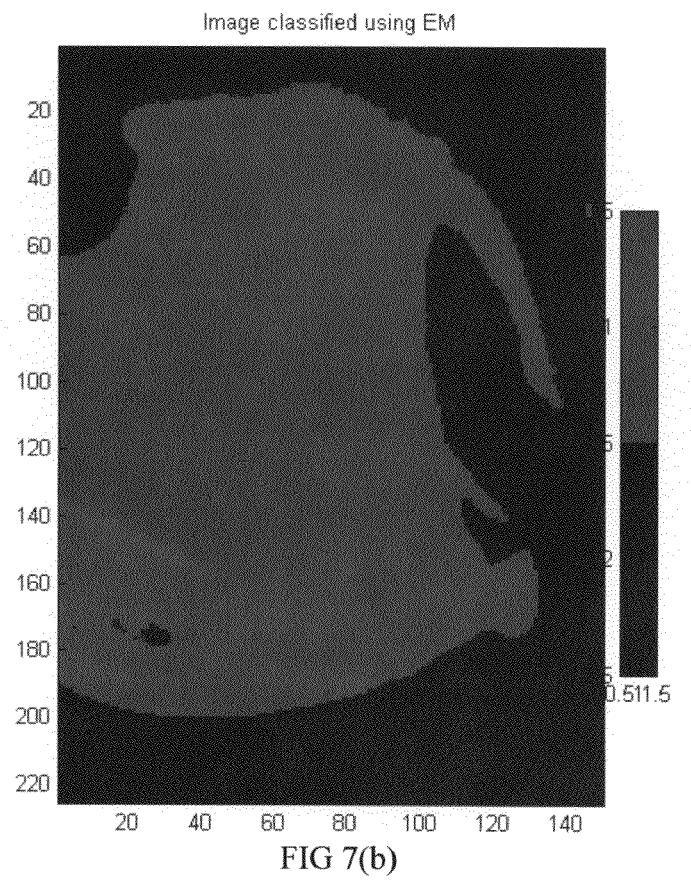

The expected hue value histogram has a peak (light gray) for the region corresponding to the cervix and vagina sidewalls, and a very close peak (dark gray) to the right of it when the body parts are outside the cervix and the vaginal sidewalls are visible, as shown in FIG. 6. Hue can be expressed as an angle vector in color space. Therefore, the histogram can be split by using the value of this angle. Instead of heuristic based thresholding (hard thresholding), which forces segmentation of all values that are lager or smaller than a threshold value, an EM algorithm (Dempster, A., Laird, N., and Rubin, D. (1977), Maximum likelihood from incomplete data via the EM algorithm, Journal of the Royal Statistical Society, Series B, 39(1):1-38, incorporated herein by reference) is preferably used as a probability based method to separate the two peaks by fitting the histogram into 2 mixture Gaussian models. The fitted Gaussian model and the classification result are shown in FIGS. 7(a) and 7(b), where FIG. 7(a) shows the fitted Gaussian model (2 classes) and FIG. 7(b) depicts the segmentation result.

Figures 8A, 8B, 8C:
FIG. 8(a), FIG. 8(b), and FIG. 8(c) show post-processing results.

After classification, the cervix region is preferably cleaned up by post-processing. First holes are closed by filling them in using a morphological operation. Then, small regions are deleted using an opening-closing ASF with reconstruction using a cross as structuring element of size 8. The results are shown in FIG. 8(a)-(c) where FIG. 8(a) shows the cervix region obtained by classification, FIG. 8(b) shows the cervix region with closed holes, and FIG. 8(c) shows the cervix region with small regions cleaned up.

3. Region Assessment

After the ROI has been detected, preferably this information is then used to assess some of the instrument settings. Poor image quality can be attributed to several factors such as:

1. Incorrect camera zooming: which makes the cervix region too small in comparison to the entire image size.
2. Incorrect camera positioning: in which the cervix region is not centered in the image.
3. Improper existence of other obstructions such as speculum or cotton swab, which will block the view of the cervix region. Certain parts of the cervix may be excluded from the field of view due to a patient's movement as well.

Figure 9A:
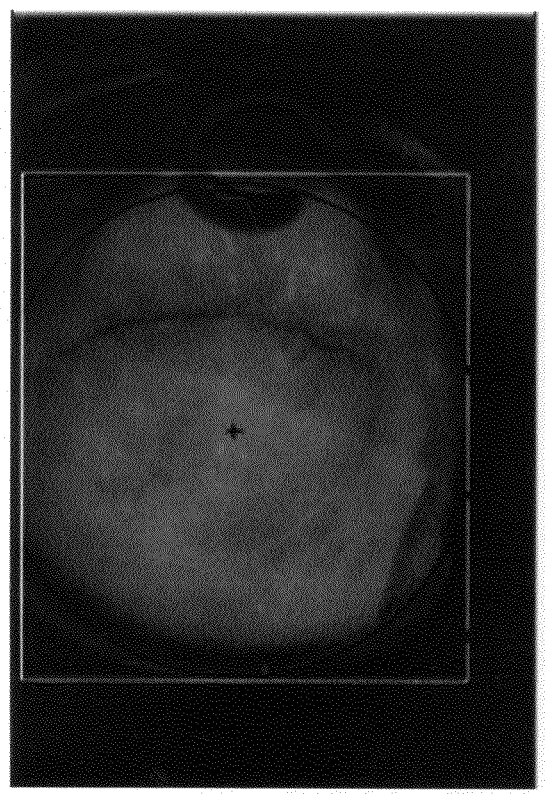
FIG. 9(a) and FIG. 9(b) show the region assessment examples. Circles represent the ellipse fitting, rectangles represent the surrounding box and the crosses represent the mass center of the cervix region.
Figure 9B:
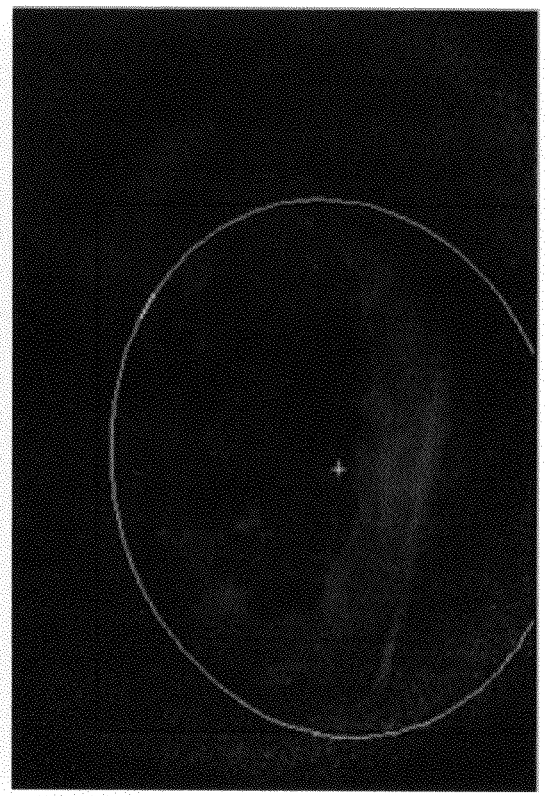

When the above circumstances occur, this system should automatically detect them and block them from entering a subsequent CAD system. Region assessment preferably consists of the following steps: (1) Fitting the detected ROI into a surrounding box; (2) calculating the dimensions and area of the surrounding box; (3) calculating the mass center of the ROI (the geometric center of the ROI) and (4) fitting the ROI to an ellipse (See FIG. 9(a) and FIG. 9(b) for examples of a cervix fitted with a box and an ellipse). The mass center of the ROI is calculated using the following integral equation:

$$\frac{\int \rho(r) r dV}{\int \rho(r) dV}$$

where $\rho(r)$ is the density function, and r is the position function. The density of a two-dimensional image of the ROI can be easily understood if you consider an ROI (with white area indicating where the cervix is located and black area indicating where the background is located, then the density function is simply 1 in the white area and 0 in the black area. The surrounding box is used to compute parameters of the fitted ellipse. The above information is then used to do region assessment based on the following criteria:

1. For the assessment of incorrect camera zooming, the ratio of the ROI area to the entire image area is preferably used. If that ratio is larger than a threshold value between approximately 0.25 to 0.45, with 0.35 being the preferred value, the camera zooming is deemed satisfactory, otherwise an error message will be displayed and notify the operator of incorrect camera zooming (See FIG. 10(a) for an example where the cervical region is too small).
2. For the assessment of incorrect camera positioning, the distance between the cervix's mass center and the image's center (the geometric center) is preferably used. If the distance is smaller than approximately 0.1 to 0.3 times the image width, with 0.2 being the preferred value, we deem that the cervix region is centered. Otherwise the camera positioning is not satisfactory (See FIG. 10(b) for an example where the cervical region is not centered).
3. For assessment of improper existence of obstructions or partially visible cervix region, the ROI is compared to the fitted ellipse (the algorithm assumes that a fully visible cervix region is elliptical or near elliptical in shape). If the difference between the ROI's area and the area of the ellipse is greater than approximately 0.2 to 0.3 times the area of the ROI (cervix region), with 0.25 being the preferred value, the cervix is deemed obstructed by the improper existence of obstacles (see FIGS. 10(c)-10(e) for examples).

4. Contrast Assessment

The purpose of the contrast assessment is to make sure the images that are taken have a satisfactory contrast. Contrast is a measure of the gradation (difference) in luminance (brightness) that provides information. Generally speaking, contrast tells us the smallest difference two nearby signals can have and still be distinguishable. A simple but robust way to assess image contrast is to do histogram analysis over the ROI. Empirically, the ROI (the cervix) is usually pinkish. The reflectance of the cervix is highest in the range of the optical spectrum corresponding to red. Therefore the quality of contrast can be assessed by analyzing the dynamic range of the red channel. The optical spectrum (also known as the visible spectrum) is the portion of the electromagnetic spectrum that is visible to the human eye. Electromagnetic radiation in this range of wavelengths is called visible light or simply light. A typical human eye will respond to wavelengths in air from about 380 to 750 nanometers (equal to one billionth of a meter). Red is any of a number of similar colors evoked by light consisting predominantly of the longest wavelengths of light discernible by the human eye, in the wavelength range of roughly 625-740 nanometer.

Figure 11A:
FIG. 11(a) and FIG. 11(b) show an example of image contrast analysis.
Figure 11B:
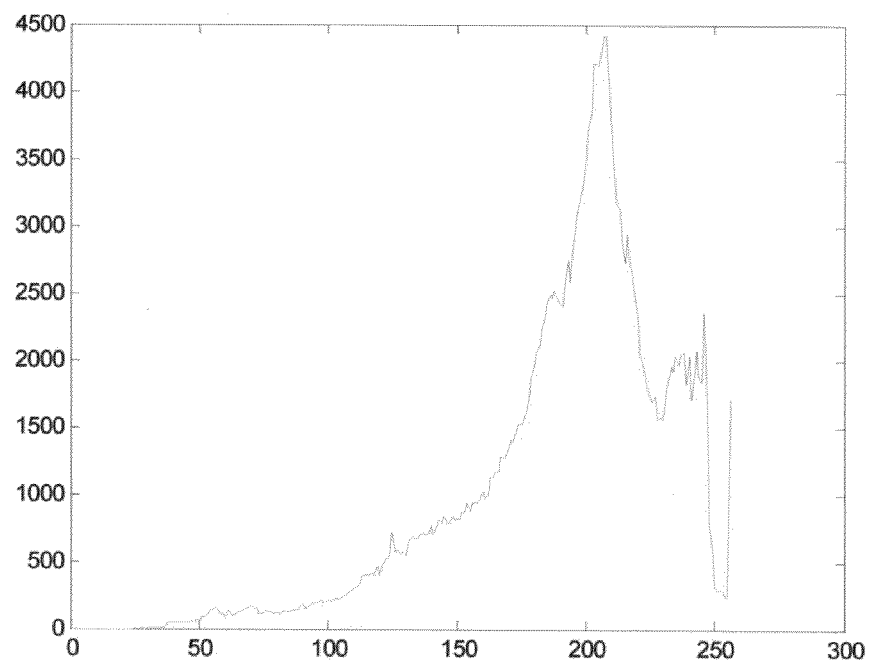

From our experiments, if the peak of the histogram in red channel is greater than $4/5$ of the full dynamic range (note that all the glints have been removed by preprocessing), the images are deemed to have satisfactory or good contrast. FIG. 11(a) and FIG. 11(b) shows an image in good contrast and its corresponding histogram.

Figure 12:
FIG. 12(a) and FIG. 12(b) show an example of false peak removal.
FIG. 12(c) Gaussian fitted histogram (preferably keeping only the rightmost peak).
Figure 12B:
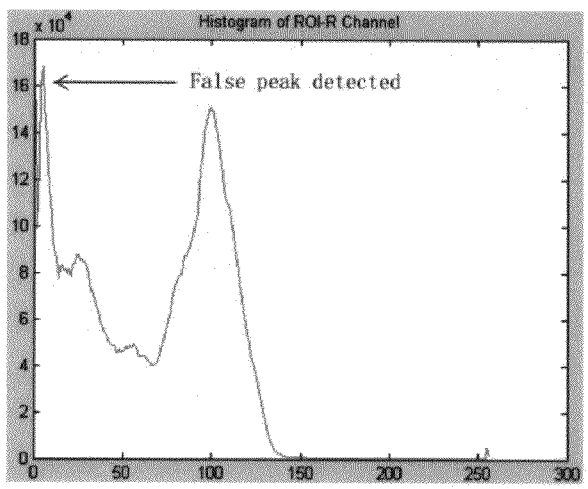
Figure 12C:
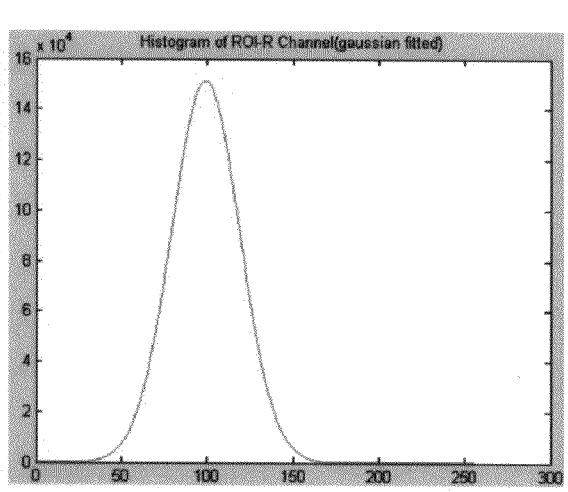

If multiple peaks exist, the assessment employs the histogram smoothing and Gaussian fitting, described in section 2.3 to smooth and remove any false peaks to provide a single-peak histogram. Thus, the assessment preferably analyzes the dynamic range by the peak farthest to the right in the R (red) channel histogram because it provides robust results. See FIG. 12(a), FIG. 12(b), and FIG. 12(c) for example. After the single-peak histogram is obtained by Gaussian fitting, the dynamic range is deemed satisfactory if the peak of the histogram is larger than $4/5$ of the full dynamic range, otherwise an error message will be displayed and notify the operator of incorrect camera contrast setting.

Alternatively, histogram analysis can be done by calculating the maximal acceptable digital number (DN) of the image compared to the optimal digital number of the camera. A DN is a positive integer value representing the relative brightness of a pixel in a digital image. The exposure time can be adjusted accordingly to make sure the image taken is of good contrast.

5. Blur Assessment

The detection of blur in images is well-investigated only if there is a reference image to compare to an input image. For example, various measurements such as entropy and Pixel Signal to Noise Ratio (PSNR) are used for determining how blurry the image is by comparing to a reference image. The presently preferred embodiment of this invention performs the blur assessment in a unique perceptual manner without the use of a reference image. The following limitations are important in the selection of a preferred algorithm: (1) no reference image is used; and (2) the various causes of image blur (e.g. the camera can be out of focus, motion blur, or a combination of the two).

Frequency-based methods make real time application possible because of their fast processing speed. The problem with most frequency-based methods is that they are sensitive to structure changes, so that an image that contains more structures but looks blurry may reflect higher quality than an image that contains less structures but has no blur at all. The presently preferred embodiment of this invention performs its blur assessment by evaluating the distribution of wavelengths by using a spatial frequency method that evaluates wavenumber frequency. Wavenumber is the spatial analog of frequency, that is, it is the measurement of the number of repeating units of a propagating wave (the number of occurrences that a wave has the same phase) per unit of space instead of per unit of time. The final step of blur assessment preferably uses a normalized image power spectrum method as the quality measure.

The algorithm can be described as the following steps:
1. Divide the image into multiple non-overlapping blocks.
2. For each block, compute a local measurement based on wave number frequency information using an image power spectrum.
3. Compute global measurement for the entire image based on the local measurements obtained from Step 2.
4. Determine whether the image is blurry or not from the global measurement.

Figure 13:
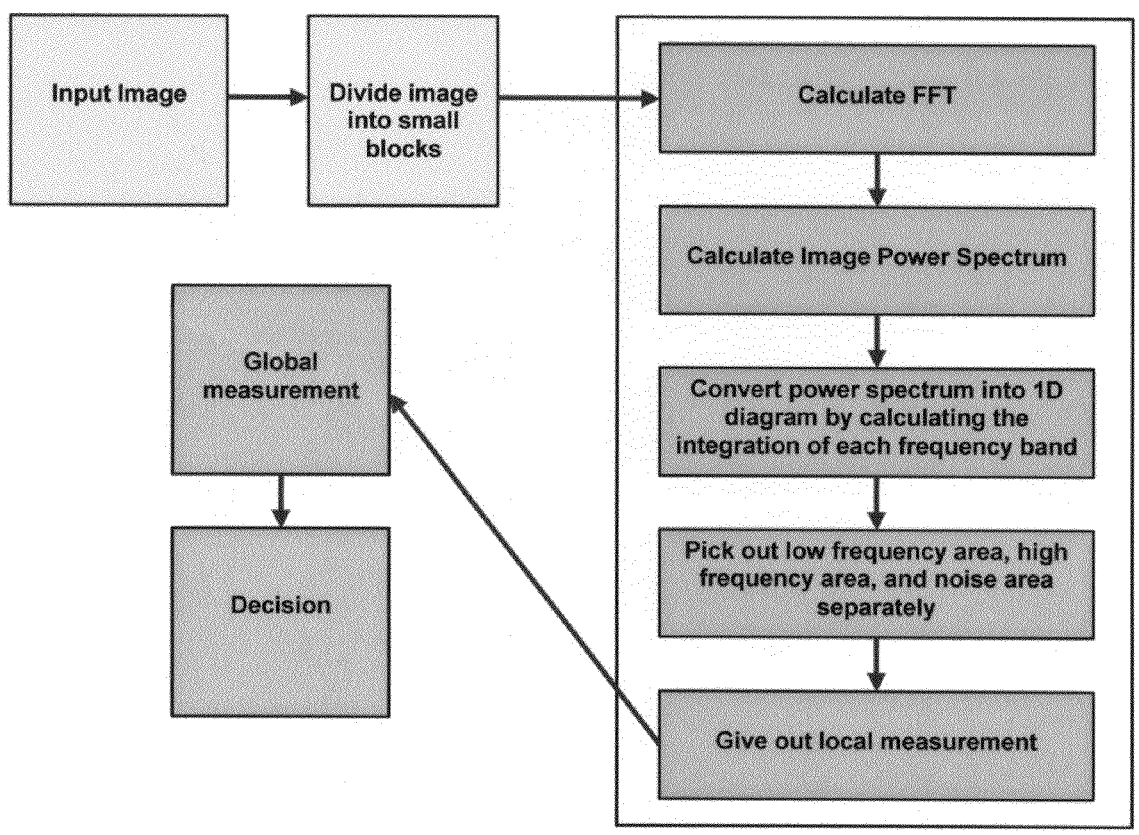
FIG. 13 shows a flowchart of the blur assessment.

A flow chart of the algorithm is depicted in FIG. 13. Note, the blocks are preferably be square, but can be of any size and spacing, as long as the distance between two blocks is not greater than approximately 20% of the length of each block.

Figure 14A:
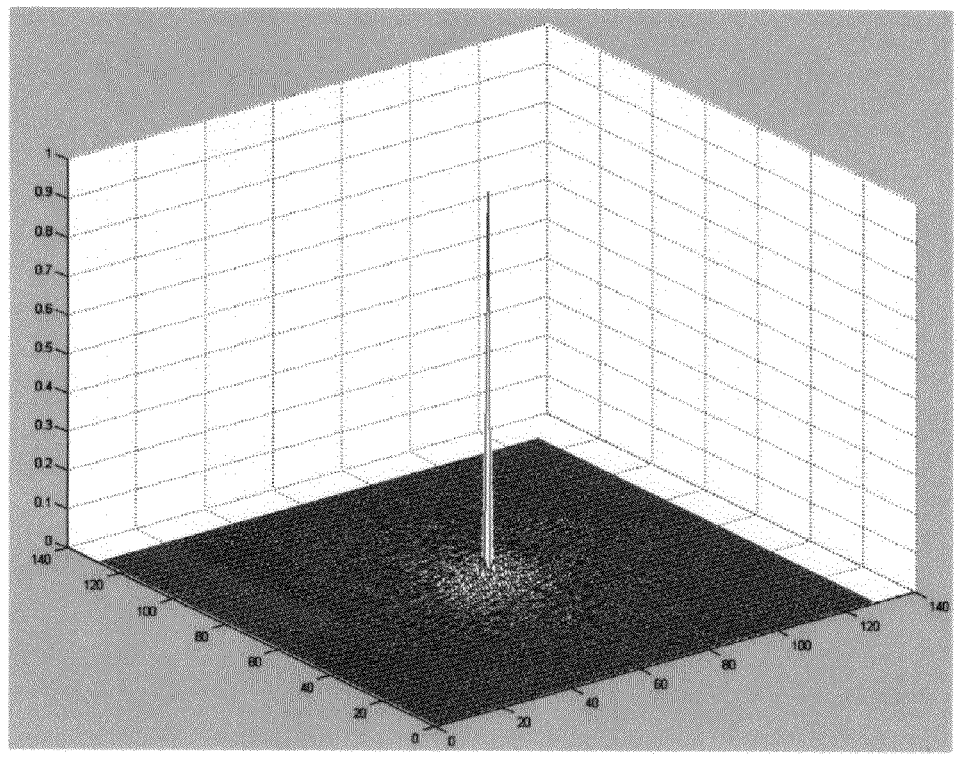
FIG. 14(a) and FIG. 14(b) shows the image power spectrum.

The local measurement of blur is calculated by image power spectrum (Nill N., Bouzas B., Objective Image quality measure derived from digital image power spectra, Optical engineering, April 1992, Vol. 31, 813-825, incorporated herein by reference) and then is normalized by the zero components, which is shown as FIG. 14(a). The term "local" refers to the fact that the calculation is limited to the area of a particular pixel in an image. The 2D image power spectrum is then transformed into a 1D diagram, by calculating the integral of all the pixels for each radius. In order to analyze the energy property in each frequency band, polar coordinate integration is used according to each radial value. See FIG.

14(*b*). In mathematics, the polar coordinate system is a two-dimensional coordinate system in which each point on a plane is determined by an angle and a distance from an origin. The polar coordinate system is especially useful in situations where the relationship between two points is most easily expressed in terms of angles and distance than the more familiar Cartesian or rectangular coordinate system, by which such a relationship can only be found through trigonometric formulae. Here radius refers to distance.

Figure 14B:
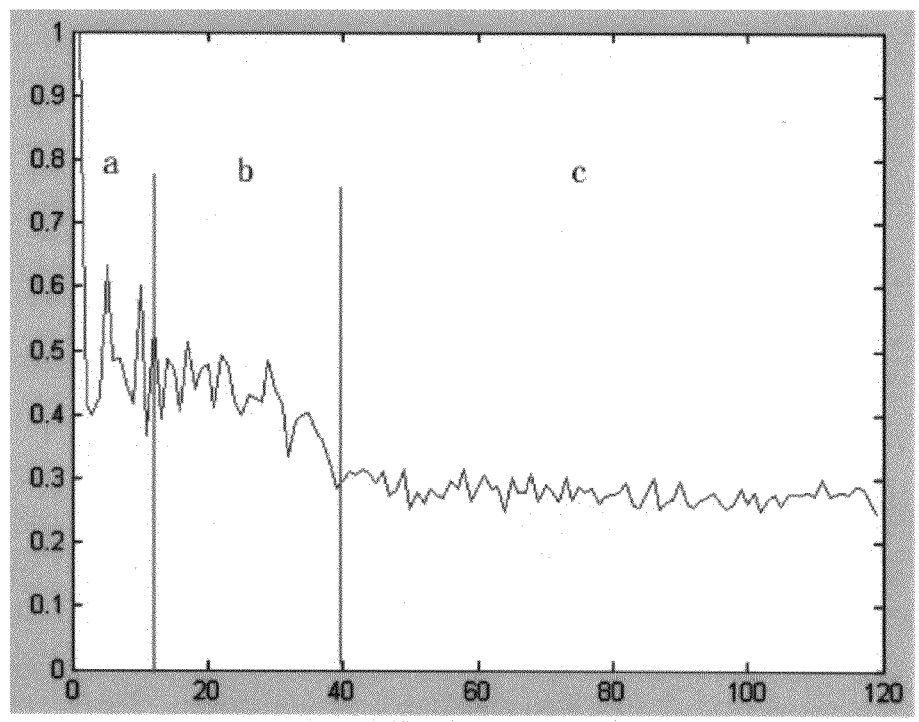

In order to determine the degree of blur without the use of a reference image, the blur assessment uses intrinsic information within the image itself. The inventors recognized that an image power spectrum can be a statistical tool for texture analysis and that the high frequency wavenumber information of the texture is always damaged in a blurred image, so the power spectrum is separated into three parts: (a) low frequency area; (b) high frequency area; and (c) noise area. The assessment assumes that the low frequency area represents structure information invariant to blur and the high frequency area represents detailed information that is more sensitive to blur (See FIG. 14(*b*) for example, where the image power spectrum 1D diagram is separated into 3 parts: (a), (b), and (c)). The degree of blur is then calculated by analyzing the ratio between the low frequency and high frequency areas. When the ratio is smaller than a threshold value, the whole block is considered blurry. The threshold is preferably 0.4 but can range from 0.3 to 0.5. Note that the noise spectrum has been discarded.

After each block is evaluated for blur, the global measurement gives out a decision as a whole by using the percentage of the number of blurred blocks in entire image. Preferably, more weight is given to those blocks in the center of the image than those in the periphery because the invention is concerned with the quality of the image at the image center (where the ROI is located). The weight is used to calculate the coverage rate. The preferred weighted method of calculating the coverage rate is preferably achieved by multiplying the number of blurry blocks in the periphery by 0.8, multiply the number of blurry blocks in the center by 1.2, adding them together, and then divide the sum by the total number of blocks.

Figure 15:
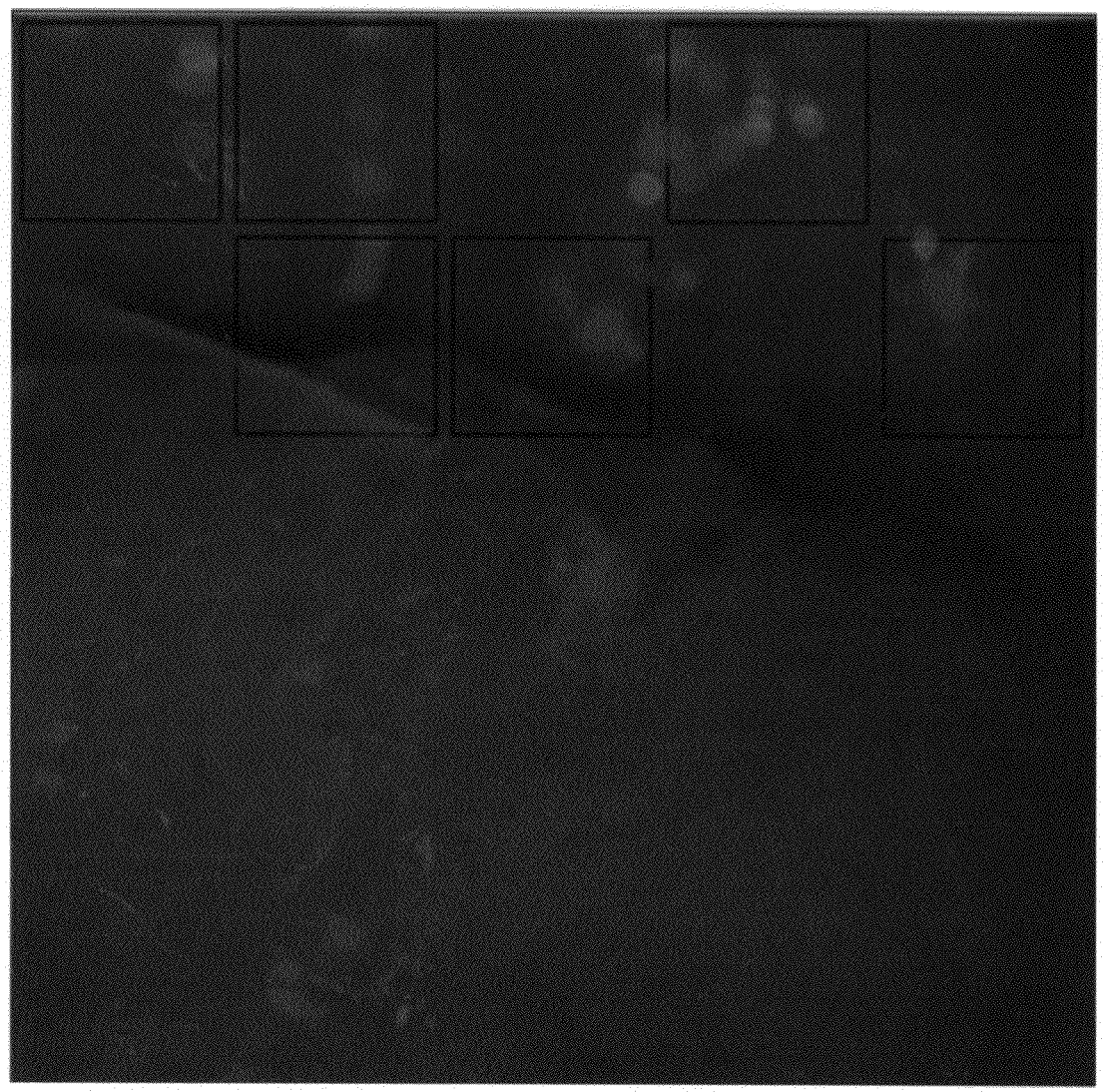
FIG. 15 shows the Blur detection result (black squares represent areas being detected as blur).

Thus, if the blurred blocks cover less than approximately 20-30% of the entire region of interest, with 25% being the preferred value, the image is deemed satisfactory (i.e. not blurry), otherwise an error message will pop up and feedback to the operator. FIG. 15 shows an example of blurred block detection in the region of interest.

Determining the focus of the cervical images can be done by two categories of methods, and they are employed for different purposes. The first method relies on a laser autofocus system in the hardware. A laser dot is projected onto the surface of the cervix at a tilted angle, and the distance between the camera and the cervix is determined using the offset of the laser dot from to the center of the image. The greater the offset, the more blurry the image is. The ideal case is that the laser is at the center. This method is preferably used in low-resolution image acquisition, which gives us a rough estimation about focus.

The second method is based on image content only, utilizing a frequency-based algorithm to detect blurred areas on the images. This method can be used in high-resolution image acquisition providing more detailed information, which can be employed to improve the performance of the CAD system.

6. Contamination Detection

Different types of contamination detection algorithms have been used in the prior art. Color and texture in both parallel-polarized (PP) and cross-polarized (XP) images are crucial information in detecting blood spot, mucus, and other types of obstruction, such as cotton swap. XP means having 2 polarizations at angles which are substantially perpendicular to each other. PP means singly-polarized or multiple polarities having polarization angles which are substantially parallel to each other.

The contamination detection in this invention preferably includes a training stage (i.e. machine learning) and a classification stage. The training stage is accomplished by a series of annotations, wherein a physician will manually mark the contamination region. Then a joint texture/color model is employed to generate the feature vector per image pixel (Chad Carson, Serge Belongie, Hayit Greenspan and Jitendra Malik, Blobworld: Enrage Segmentation Using Expectation-Maximization and Its Application to Image Querying; *IEEE Trans. on Pattern Analysis and Machine Intelligence*, 24(8), 1026-1038, August 2002, incorporated herein by reference). Finally a Support Vector Machine (SVM) algorithm is used to detect contamination in the cervical images (Chang C. and Lin J. Training nu-support vector regression: theory and algorithms, Neural Computation, 14 (2002), 1959-1977, incorporated herein by reference). SVMs generally are a set of related supervised learning methods used for classification and regression.

The training process uses 3 color features and 3 texture features. The 3 color components are preferably the L*a*b* coordinates found after spatial averaging using a Gaussian filter, and the 3 texture components are preferably anisotropy, polarity and contrast (Zhang J., Liu Y., Zhao T., SVM Based Feature Screening Applied to Hierarchical Cervical Cancer Detection, International Conference on Diagnostic Imaging and Analysis (ICDIA 2002), August, 2002, incorporated herein by reference). However, instead of using an EM algorithm as unsupervised clustering, an SVM algorithm as supervised classification is preferably utilized, due to adequate, accurate annotation. Some preliminary results of the blood detection are provided here. Furthermore, for other kinds of contamination detection such as mucus and purulence, similar algorithms can be designed if the annotation is precise and adequate. FIG. 16 shows some experimental results on blood detection.

While the present invention has been particularly shown and described with reference to embodiments described in the detailed description and illustrated in the figures, it will be understood by one skilled in the art that various changes in detail may be effected therein without departing from the spirit and scope of the invention, as defined by the claims. Accordingly, no limitations are to be implied or inferred except as explicitly set forth in the claims.

INDUSTRIAL APPLICABILITY

The assessment algorithms of the invention may also be suitable for image quality assessment for other tissue diagnosis such as colorectal cancer and skin cancer, and could be used for telemedicine applications. They may also be combined with other instruments and methods for systems that automatically analyze and adjust the quality of acquired images.

What is claimed is:
1. A method of image quality assessment to produce standardized images for use in archive-quality electronic medical records and in CAD systems comprising:
    collecting a raw image free from glare during an examination with a digital imager, wherein said raw image contains a region of interest having borders, a border length and a border width, that define an image area within said borders, and an image center, and wherein said region of interest contains a region of interest area and a region of interest mass center;

locating said region of interest using an image classification algorithm;

applying a region assessment to said region of interest to detect incorrect camera zooming, incorrect camera positioning, and obstructions;

performing a contrast assessment on said region of interest using a histogram-based algorithm that generates a contrast histogram having peaks, ranges, and channels, including a red channel, and determining whether said contrast assessment is satisfactory from peaks of said contrast histogram in said red channel;

running a blur assessment without a reference image, wherein said blur assessment step comprises dividing said region of interest into non-overlapping blocks, computing a local measurement for each of said blocks based on frequency information using an image power spectrum to produce a two-dimensional display of said image power spectrum, converting said two-dimensional display to a one-dimensional display, separating said one-dimensional display into a low frequency area, a high frequency area and a noise area, and determining a degree of blur for each of said bocks by calculating the ratio of said low-frequency area to said high-frequency area, and using said degree of blur to determine if said block is a blurred block;

determining the percentage of blurred blocks to determine if said image is blurry; and using contamination detection to detect obstructions using a training stage and a classification algorithm to produce said standardized images.

2. A method according to claim 1, wherein said locating step comprises transforming said raw image into an HSI image having hue values, creating a hue histogram of said hue values wherein said hue histogram contains peaks, ranges for said peaks, a dynamic range, and a median value for said dynamic range; shifting said hue histogram by the median value of the dynamic range; smoothing said hue histogram using filters; performing classification using an EM algorithm; and applying post processing.

3. A method according to claim 1, wherein said region assessment step comprises fitting said region of interest into a surrounding box; calculating said region of interest mass center; fitting said region of interest area to an ellipse having an ellipse area; detecting said incorrect camera zooming by calculating a zoom ratio between said region of interest area to said image area; detecting said incorrect camera positioning by calculating a distance between said region of interest mass center and said image center; and detecting said obstructions by comparing differences between said region of interest area and said ellipse area.

4. A method according to claim 1, wherein said contrast assessment is performed using a histogram based algorithm that generates a contrast histogram having peaks, ranges, and channels, including red channels, and wherein said contrast assessment is satisfactory if said contrast histogram peak farthest to the right in said red channel is greater than approximately 4/5 of said contrast histogram's range.

5. A method according to claim 1, wherein each of said blocks is a blurred block if said ratio is less than approximately 0.3-0.5, and wherein said blur assessment is satisfactory if each of said blurred blocks covers less than approximately 20-30% of said region of interest area.

6. A method according to claim 1, wherein said training stage comprises the steps of machine learning with a series of annotations; applying a joint texture/color model to produce a feature vector per image pixel; and applying classification algorithm to detect contamination.

7. A method according to claim 3, wherein said camera zooming is satisfactory when said zoom ratio of said region of interest area to said image area is greater than approximately 0.25-0.45.

8. A method according to claim 3, wherein said camera positioning is satisfactory when said distance between said region of interest mass center and said image center is less than approximately 0.1-0.3 times said border width.

9. A method according to claim 3, wherein said obstructions exist if said difference between said region of interest area and said ellipse area is larger than 0.2-0.3 times said region of interest area.

10. A method according to claim 6, wherein said joint texture/color model uses three color features and three texture features, and wherein said classification algorithm is a Support Vector Machine.

11. A method of image quality assessment to produce standardized images for use in archive-quality electronic medical records and in CAD systems comprising:

collecting a raw image free from glare during an examination with a digital imager, wherein said raw image contains a region of interest having borders, a border length and a border width, that define an image area within said borders, and a image center, and wherein said region of interest contains a region of interest area and a region of interest mass center;

locating said region of interest using an image classification algorithm by transforming said raw image into an HSI image having hue values, creating a hue histogram of said hue values wherein said hue histogram contains peaks, ranges for said peaks, a dynamic range, and a median value for said dynamic range; shifting said hue histogram by the median value of the dynamic range; smoothing said hue histogram using filters; performing classification using an EM algorithm; and applying post processing;

applying a region assessment to said region of interest to detect incorrect camera zooming, incorrect camera positioning, and obstructions by fitting said region of interest into a surrounding box; calculating said region of interest mass center; fitting said region of interest area to an ellipse having an ellipse area; detecting said incorrect camera zooming by calculating a zoom ratio between said region of interest area to said image area; detecting said incorrect camera positioning by calculating a distance between said region of interest mass center and said image center; and detecting said obstructions by comparing differences between said region of interest area and said ellipse area;

performing a contrast assessment on said region of interest using a histogram-based algorithm that generates a contrast histogram having peaks, ranges, and channels, including red channels, and wherein said contrast assessment is satisfactory if said contrast histogram peak farthest to the right in said red channel is greater than approximately 4/5 of said contrast histogram's range;

running a blur assessment without a reference image, wherein said blur assessment step comprises dividing said region of interest into non-overlapping blocks, computing a local measurement for each of said blocks based on frequency information using an image power spectrum to produce a two-dimensional display of said image power spectrum, converting said two-dimensional display to a one-dimensional display, separating said one-dimensional display into a low frequency area, a high frequency area and a noise area, and determining a degree of blur for each of said bocks by calculating the ratio of said low-frequency area to said high-frequency area, and using said degree of blur to determine if said block is a blurred block;

determining the percentage of blurred blocks to determine if said image is blurry; and using contamination detection to detect obstructions using a training stage that utilizes machine learning with a series of annotations; applying a joint texture/color model to produce a feature vector per image pixel; and applying a Support Vector Machine to detect contamination and producing said standardized images.

\* \* \* \* \*